(12) United States Patent
Kwon et al.

(10) Patent No.: US 6,337,150 B1
(45) Date of Patent: Jan. 8, 2002

(54) LIGHT-EMITTING COMPOUND AND DISPLAY DEVICE ADOPTING LIGHT-EMITTING COMPOUND AS COLOR-DEVELOPING SUBSTANCE

(75) Inventors: Soon-ki Kwon, Chinju; Yun-hi Kim, Pusan; Dong-cheol Shin, Chinju; Jun-hwan Ahn, Kwangju; Han-sung Yu, Anyang; Sung-hyun Cho, Seoul, all of (KR)

(73) Assignee: Samsung Display Devices Co., Ltd., Kyungki-Do (KR)

(*) Notice: Subject to any disclaimer, the term of this patent is extended or adjusted under 35 U.S.C. 154(b) by 0 days.

(21) Appl. No.: 09/280,561

(22) Filed: Mar. 30, 1999

(30) Foreign Application Priority Data

Nov. 12, 1998 (KR) ............................................. 98-48404

(51) Int. Cl.[7] ........................ B32B 19/00; C09K 11/06; H01J 1/62

(52) U.S. Cl. .................. 428/690; 428/917; 252/301.16; 252/301.35; 313/110; 313/504; 313/506; 313/507

(58) Field of Search ................................ 428/690, 917; 252/301.16, 301.35; 313/504, 506, 507, 110

(56) References Cited

U.S. PATENT DOCUMENTS 5,486,441 A * 1/1996 Matsushima et al. ......... 430/74
5,503,910 A * 4/1996 Matsuura et al. ............ 428/212

* cited by examiner

Primary Examiner—Samuel A. Acquah
(74) Attorney, Agent, or Firm—Lowe Hauptman Gilman & Berner

(57) ABSTRACT

A light-emitting compound and a display device adopting the light-emitting compound as a color-developing substance. When the display device adopts an organic layer formed of such light-emitting compound as a blue light-emitting material, luminous efficiency of the display device is improved.

22 Claims, 13 Drawing Sheets

LIGHT-EMITTING COMPOUND AND DISPLAY DEVICE ADOPTING LIGHT-EMITTING COMPOUND AS COLOR-DEVELOPING SUBSTANCE

BACKGROUND OF THE INVENTION

1. Field of the Invention

The present invention relates to a blue light-emitting compound and a display device adopting the light-emitting compound as a color-developing substance.

2. Description of the Related Art

Recent advances in the information and communications industries have increased the need for high performance display devices. Generally, display devices are classified into luminous types and non-luminous types. Luminous type display devices include cathode ray tube (CRT) and light emitting diode (LED), and non-luminous type display device include liquid crystal display (LCD).

As an index of the basic performance of the display device, there are operating voltage, power consumption, luminance, contrast, response time, life span and display color, among others.

The LCD, as one of the non-luminous type display device, has been most favored recently, due to its light weight and low power consumption. However, characteristics such as response time, contrast and viewing angle properties are unsatisfactory, leaving room for improvement. Meanwhile, an electro-luminescence (EL) device has been a focus of attention as a next generation display device which can solve such problems.

The EL device as a spontaneous luminous type display has a broad viewing angle, a good contrast characteristic and a rapid response time. The EL devices are classified into an inorganic EL device and an organic EL device depending on the material used for a light-emitting layer. In particular, the organic EL device has good luminance, driving voltage and response time characteristic and can display a multitude of colors, compared to the inorganic EL device.

FIG. 1 is a section view showing the structure of a general EL device. Referring to FIG. 1, an anode 12 is formed on a substrate 11. A hole transport layer 13, a light-emitting layer 14, an electron transport layer 15, and a cathode 16 are formed on the anode 12 in sequence. Here, the hole transport layer 13, the light-emitting layer 14 and the electron transport layer 15 are organic thin films formed of an organic compound.

The organic EL device having the above structure operates based on the following operation principle. When a voltage is applied between the anode 12 and the cathode 16, holes injected from the anode 12 move through the hole transport layer 13 to the light-emitting layer 14. Meanwhile, electrons are injected from the cathode 16 through the electron transport layer 15 to the light-emitting layer 14. Also, carriers are recoupled in the light-emitting layer 14 to generate exitons. The exitons are transited from an excited state to a ground state, so that fluorescent molecules of the light-emitting layer emit light to form a picture.

Also, an organic EL device adopting an aromatic diamine and aluminum complex having a low molecular weight has been developed by Eastman Kodak Company (*Appl. Phys. Lett.* 51, 913, 1987) In addition, an organic EL device adopting a polymer such as poly(p-phenylenevinylene) (PPV) or poly(2-methoxy-5-(2'-ethylhexyloxy)-1,4-phenylenevinylene) as a material for a light-emitting layer has been disclosed (*Nature,* 347, 539, 1990, and *Appli. Phys. Lett.* 58, 1982, 1991). However, PPV among the polymers has a poor solubility in an organic solvent, so that it is difficult to adopt a spin-coating so as to form a film by spin-coating method. To solve this problem, a soluble PPV having a functional group capable of improving its solubility in an organic solvent has been developed. The organic EL device having a light-emitting layer formed of PPV or a derivative of the PPV displays a multitude of colors from green to orange.

Also, blue light-emitting compounds known thus far are low in luminous efficiency compared to other colors of light-emitting compound. Thus a need for a new blue light-emitting compound having a high luminous efficiency has increased.

Accordingly, a compound having a non-conjugative spacer group such as silicon (Si) or oxygen (O) between luminous groups of PPV, as a blue light-emitting compound, has been suggested. However, a light-emitting layer formed of the light-emitting compounds is not satisfactory in characteristics such as a film strength.

SUMMARY OF THE INVENTION

It is an object of the present invention to provide a new blue light-emitting compound capable of solving the problems.

It is another object of the present invention to provide a display device adopting the blue light-emitting compound as a color-developing substance.

To achieve the first object of the present invention, there is provided a light-emitting compound represented by the chemical formula (1):

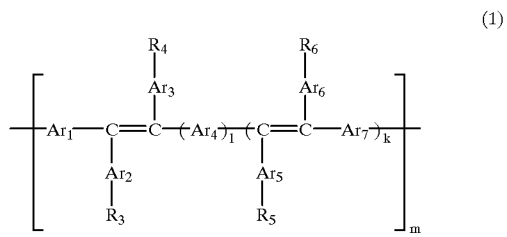

wherein $Ar_1$, $Ar_2$, $Ar_3$, $Ar_5$, $Ar_6$ and $Ar_7$ are independently selected from the group consisting of chemical bond, unsubstituted or substituted phenyl, unsubstituted or substituted naphthalene, unsubstituted or substituted anthracene, unsubstituted or substituted diphenylanthracene, unsubstituted or substituted phenanthrene, unsubstituted or substituted indene, unsubstituted or substituted acenaphtene, unsubstituted or substituted biphenyl, unsubstituted or substituted fluorene, unsubstituted or substituted carbazole, unsubstituted or substituted thiophene, unsubstituted or substituted pyridine, unsubstituted or substituted oxadiazole, unsubstituted or substituted oxazole, unsubstituted or substituted triazole, unsubstituted or substituted benzothiophene, unsubstituted or substituted dibenzofuran, and unsubstituted or substituted thiadiazole; $Ar_4$ is selected from the group consisting of unsubstituted or substituted phenyl, unsubstituted or substituted biphenyl, unsubstituted or substituted thiophene, unsubstituted or substituted pyridine, unsubstituted or substituted oxadiazole, unsubstituted or substituted oxazole, unsubstituted or substituted triazole, and unsubstituted or substituted thiadiazole; $R_1$, $R_2$, $R_2$, $R_4$, $R_5$ and $R_6$ are independently selected from the group consisting of hydrogen, ethyleneoxyalkyl group, $C_1$–$C_{20}$ alkyl group, $C_1$–$C_{20}$ alkoxy group, aryl group, trimethylsilyl group, and trimethylsilylaryl group; l and k are independently 0 or 1; and m is an integer from 10 to 200.

The second object of the present invention is achieved by a display device adopting the light-emitting compound as a color-developing substance. Preferably, the display device is an organic electro-luminescence (EL) device adopting the light-emitting compound as a color-developing substance.

To achieve the second object of the present invention, there is provided an organic electro-luminescence device comprising an organic layer between a pair of electrodes, wherein the organic layer comprises a light-emitting compound represented by the chemical formula (1):

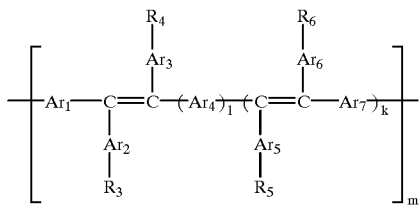

(1)

wherein $Ar_1$, $Ar_2$, $Ar_3$, $Ar_5$, $Ar_6$ and $Ar_7$ are independtly selected from the group consisting of chemical bond, unsubstituted or substituted phenyl, unsubstituted or substituted naphthalene, unsubstituted or substituted anthracene, unsubstituted or substituted diphenylanthracene, unsubstituted or substituted phenanthrene, unsubstituted or substituted indene, unsubstituted or substituted acenaphtene, unsubstituted or substituted biphenyl, unsubstituted or substituted fluorene, unsubstituted or substituted carbazole, unsubstituted or substituted thiophene, unsubstituted or substituted pyridine, unsubstituted or substituted oxadiazole, unsubstituted or substituted oxazole, unsubstituted or substituted triazole, unsubstituted or substituted benzothiophene, unsubstituted or substituted dibenzofuran, and unsubstituted or substituted thiadiazole; $Ar_4$ is selected from the group consisting of unsubstituted or substituted phenyl, unsubstituted or substituted biphenyl, unsubstituted or substituted thiophene, unsubstituted or substituted pyridine, unsubstituted or substituted oxadiazole, unsubstituted or substituted oxazole, unsubstituted or substituted triazole, and unsubstituted or substituted thiadiazole; $R_1$, $R_2$, $R_3$, $R_4$, $R_5$ and $R_6$ are independently selected from the group consisting of hydrogen, ethyleneoxyalkyl group, $C_1$–$C_{20}$ alkyl group, $C_1$–$C_{20}$ alkoxy group, aryl group, trimethylsilyl group, and trimethylsilylaryl group; l and k are independently 0 or 1; and m is an integer from 10 to 200.

Preferably, $Ar_1$ is represented by the following structural formula:

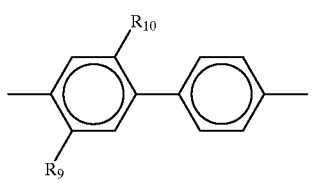

; $R_9$ and $R_{10}$ are independently a $C_1$–$C_{20}$ alkyl group or $C_1$–$C_{20}$ alkoxy group.

Preferably, $Ar_7$ is represented by the following structural formula:

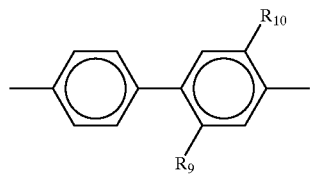

; $R_9$ and $R_{10}$ are independently a $C_1$–$C_{20}$ alkyl group or $C_1$–$C_{20}$ alkoxy group.

Also, preferably, $Ar_2$ is represented by the following structural formula:

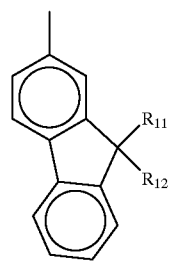

; $R_{11}$ and $R_{12}$ are independently a $C_1$–$C_{20}$ alkyl group, phenyl group or alkylsilyl group.

BRIEF DESCRIPTION OF THE DRAWINGS

The above objects and advantages of the present invention will become more apparent by describing in detail preferred embodiments thereof with reference to the attached drawings in which.

DESCRIPTION OF THE PREFERRED EMBODIMENTS

Figure 1:
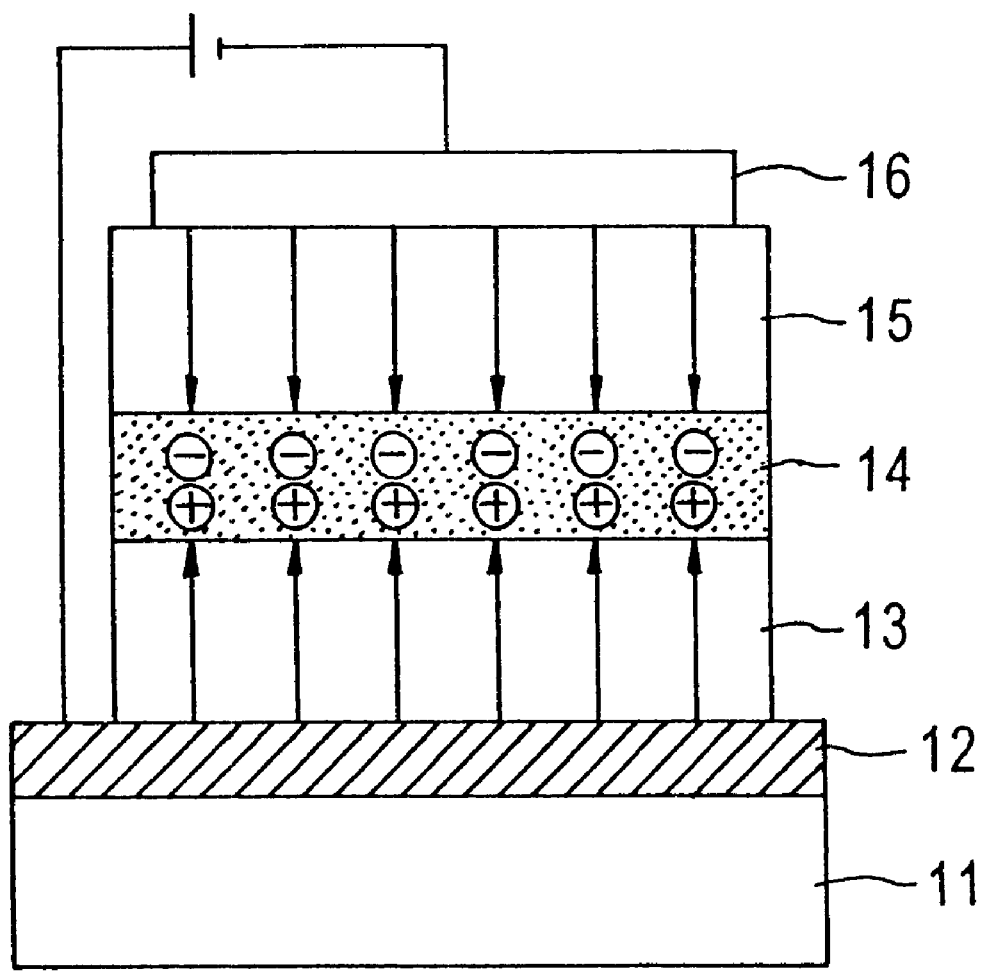
FIG. 1 is a section view showing the structure of a general organic electro-luminecence (EL) device.
Figure 2:
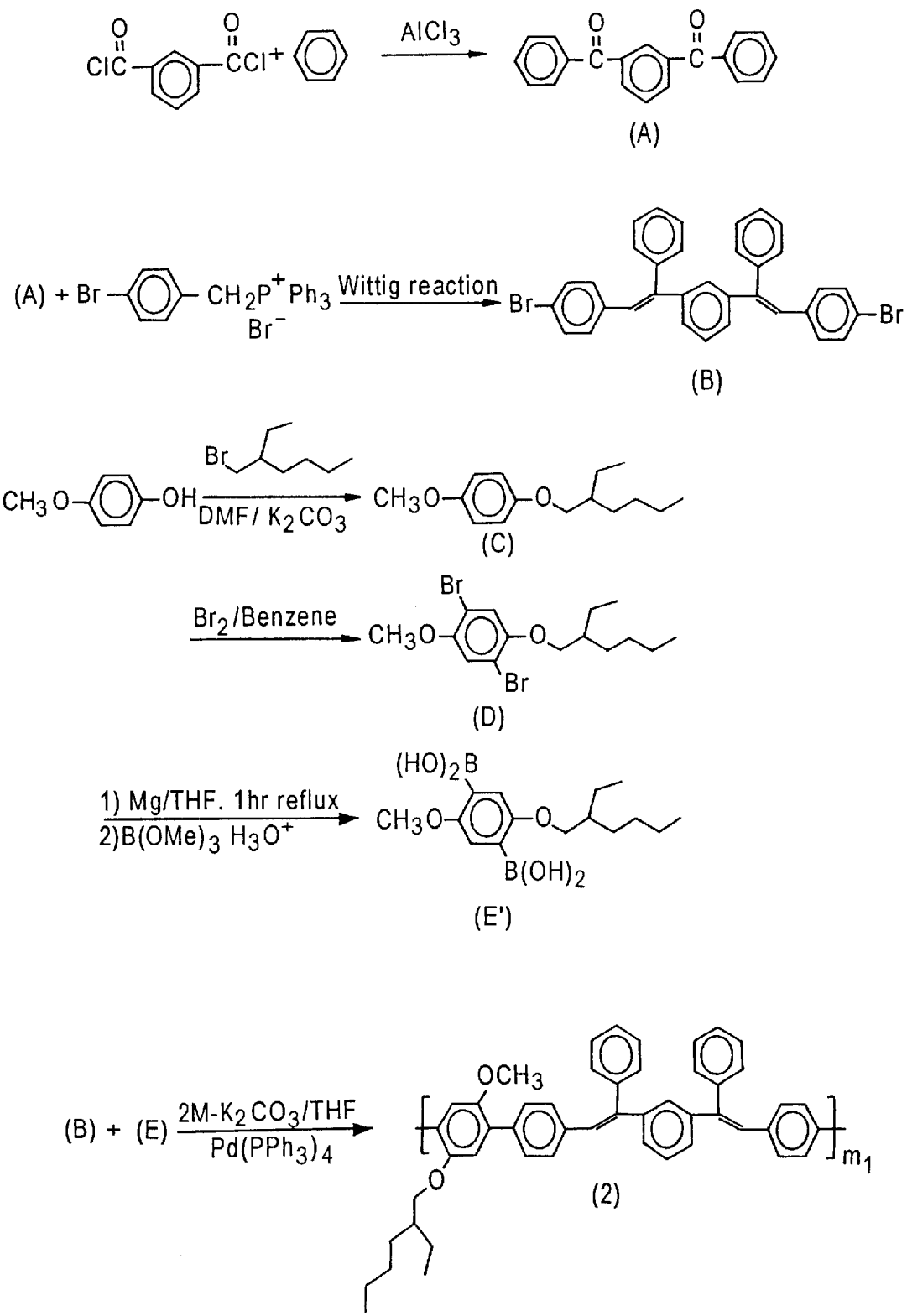
FIGS. 2 through 5 illustrate the process of synthesizing the compounds represented by chemical formulae (2) through (5), respectively.
Figure 3:
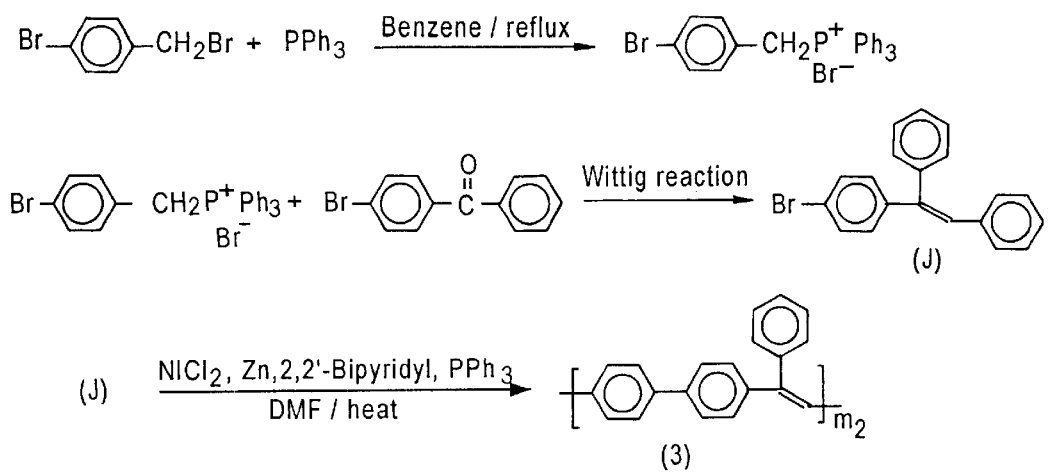
Figure 4:
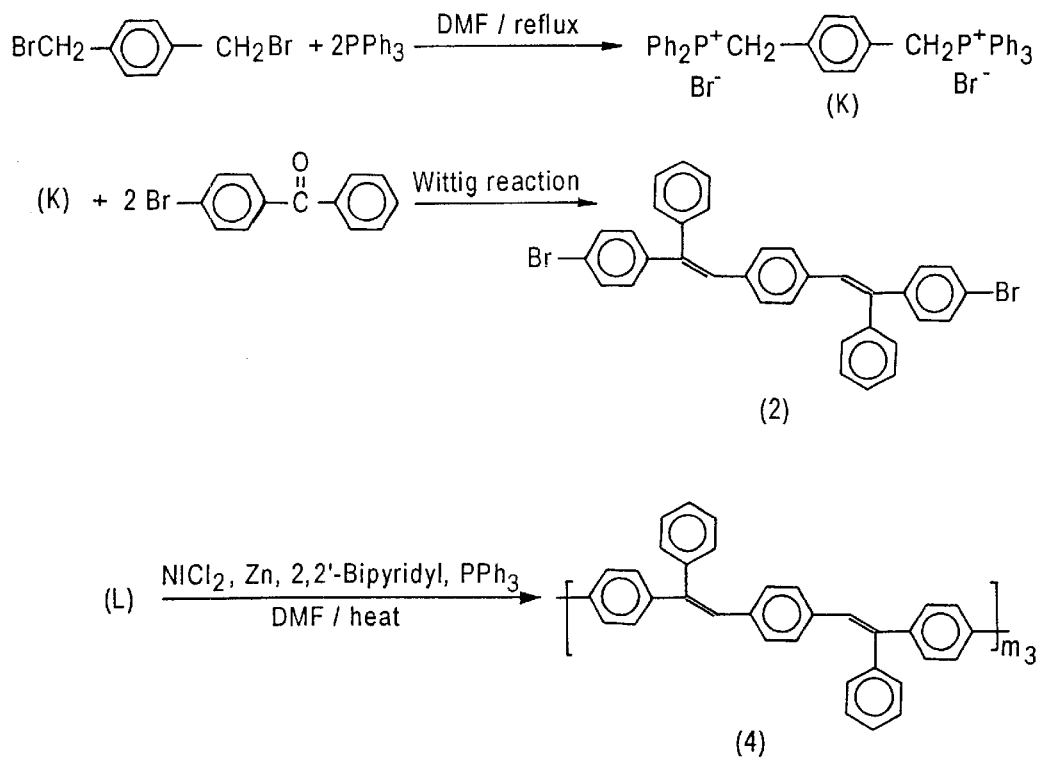
Figure 5:
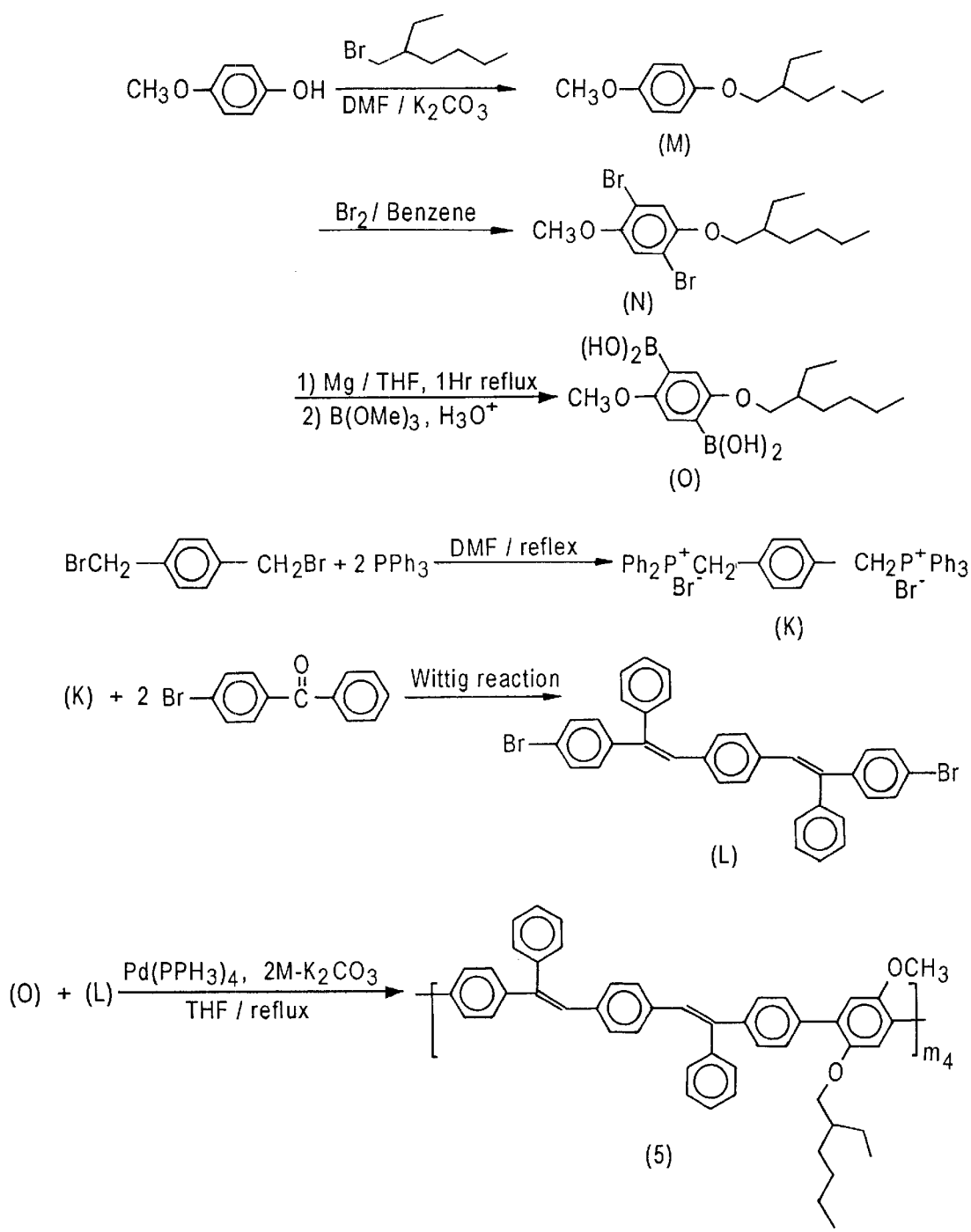
Figure 6:
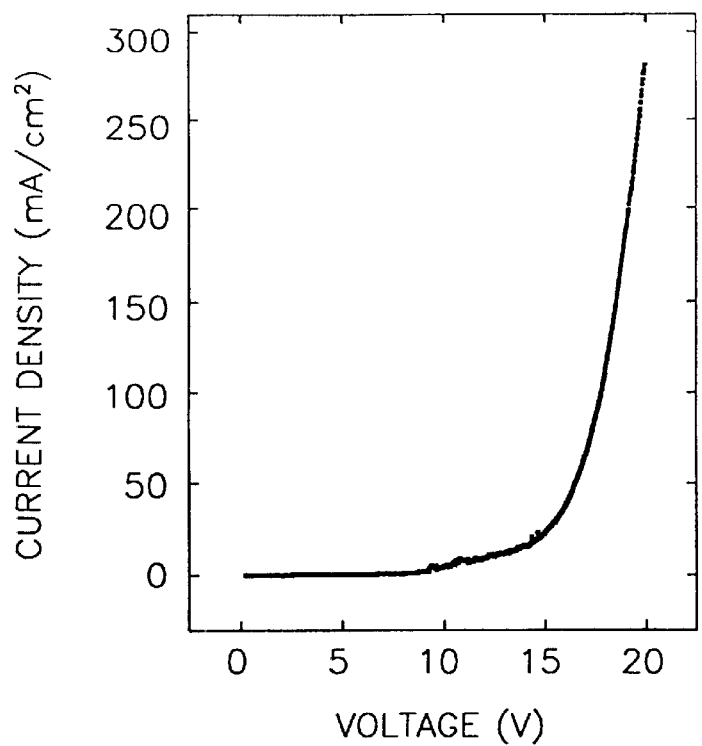
FIGS. 6, 8, 9, 11, 12, 15, 17, 19 and 21 are graphs showing the changes in current density according to voltage in the organic EL devices manufactured in Examples 1 through 12.
Figure 7:
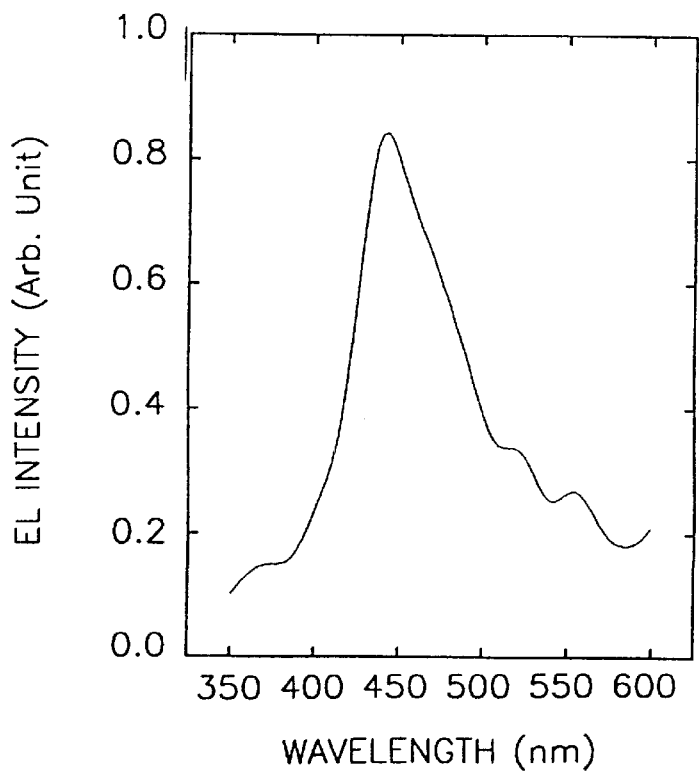
FIGS. 7, 10, 13, 14, 16, 18, 20 and 22 are graphs showing emission spectra of the organic electro-luminescence (EL) devices manufactured in Examples 1, 5, 6, 7, 8, 9, 10, 11 and 12.
Figure 8:
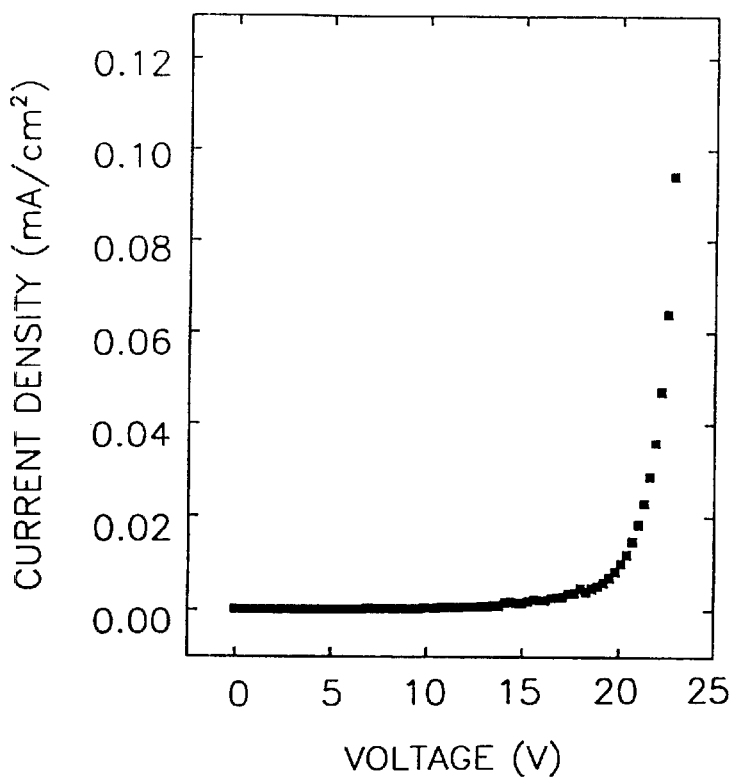
Figure 9:
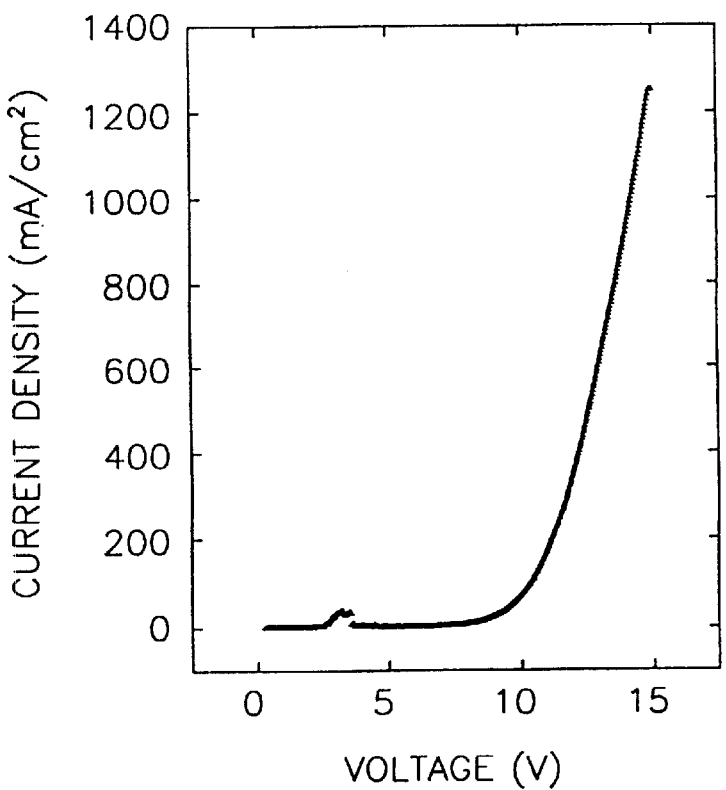
Figure 10:
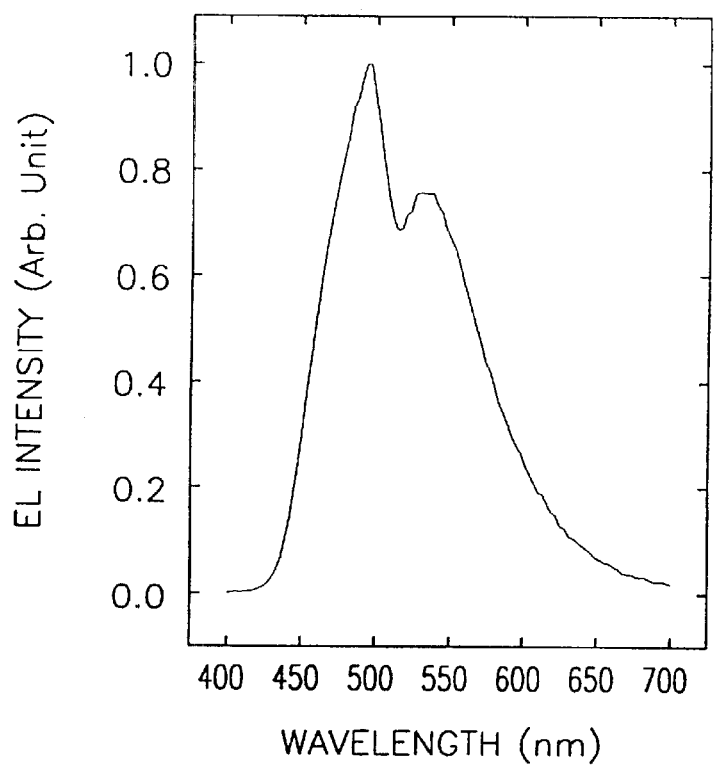
Figure 11:
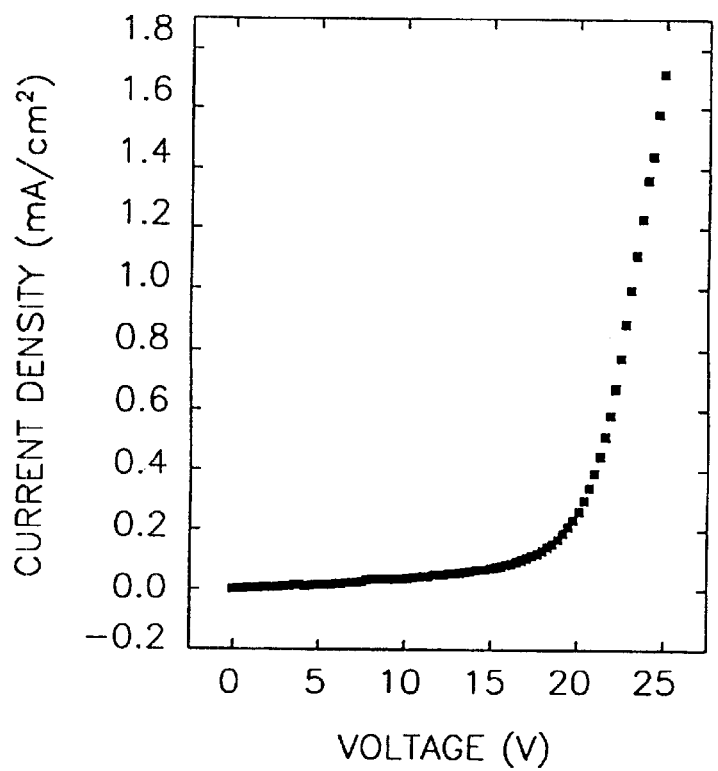

A light-emitting compound according to the present invention, represented by the following chemical formula (1), is a fully-aromatic poly(p-phenylenevinylene) (PPV) series polymer which emits the blue color. Such light-emitting compound is useful as a color-developing substance for a display device, in particular, for an organic electro-luminescence (EL) device.

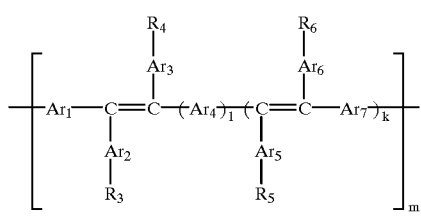

(1)

In the chemical formula (1), $Ar_1$, $Ar_2$, $Ar_3$, $Ar_5$, $Ar_6$ and $Ar_7$ are independtly selected from the group consisting of chemical bond, unsubstituted or substituted phenyl, unsubstituted or substituted naphthalene, unsubstituted or substituted anthracene, unsubstituted or substituted diphenylanthracene, unsubstituted or substituted phenanthrene, unsubstituted or substituted indene, unsubstituted or substituted acenaphtene, unsubstituted or substituted biphenyl, unsubstituted or substituted fluorene, unsubstituted or substituted carbazole, unsubstituted or substituted thiophene, unsubstituted or substituted pyridine, unsubstituted or substituted oxadiazole, unsubstituted or substituted oxazole, unsubstituted or substituted triazole, unsubstituted or substituted benzothiophene, unsubstituted or substituted dibenzofuran, and unsubstituted or substituted thiadiazole; $Ar_4$ is selected from the group consisting of unsubstituted or substituted phenyl, unsubstituted or substituted biphenyl, unsubstituted or substituted thiophene, unsubstituted or substituted pyridine, unsubstituted or substituted oxadiazole, unsubstituted or substituted oxazole, unsubstituted or substituted triazole, and unsubstituted or substituted thiadiazole, $R_1$, $R_2$, $R_3$, $R_4$, $R_5$ and $R_6$ are independently selected from the group consisting of hydrogen, ethyleneoxy group, $C_1$–$C_{20}$ alkyl group, $C_1$–$C_{20}$ alkoxy group, aryl group, trimethylsilyl group, and trimethylsilylaryl group; l and k are independently 0 or 1; and m is an integer from 10 to 200.

In the chemical formula (1), the example of the substituted phenyl includes methoxyphenyl, methylphenyl, triphenylsilylphenyl and ethylhexyloxyphenyl, the example of the substituted naphthalene includes methoxynaphthalene and phenylnaphthalene, the example of the substituted anthracene includes phenylanthracene, the example of the substituted diphenylanthracene includes 2-phenoxy-9,10-diphenylanthracene, the example of the substituted phenanthrene includes phenylphenanthrene, the example of the substituted indene includes dihexylindene, the example of the substituted acenaphtene includes phenylacenaphtene, the example of the substituted biphenyl includes methoxybiphenyl and phenoxybiphenyl, the example of the substituted fluorene includes dimethylfluorene, diethylfluorene, dipropylfluorene, dibutylfluorene, dipentylfluorene, dihexylfluorene, diheptylfluorene, dioctylfluorene, dinonylfluorene, didecylfluorene, didodecylfluorene and diphenyl fluorene, the example of the substituted carbazole includes N-ethylhexylcarbazole, the example of the substituted thiophene includes 5-phenylthiophene, the example of the substituted pyridine includes phenylpyridine, the example of the substituted oxadiazole includes phenyloxadiazole and diphenyloxadiazole, the example of the substituted oxazole includes benzooxazole, the example of the substituted triazole includes 2,5-dipheyl-1-(3'-trifluoromethylphenyl)triazole, the example of the substituted benzothiophene includes phenylbenzothiophene, the example of the substituted dibenzofuran includes phenyldibenzofuran, and the example of the substituted thiadiazole includes phenylthiadiazole and diphenylthiadiazole.

For example, the compound represented by the chemical formula (1) according to the present invention may be compounds represented by chemical formulae (2) through (6).

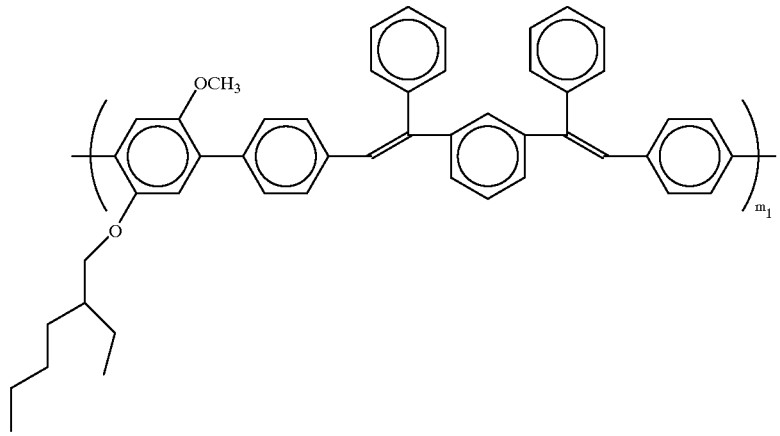

(2)

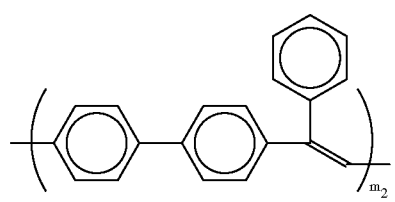

(3)

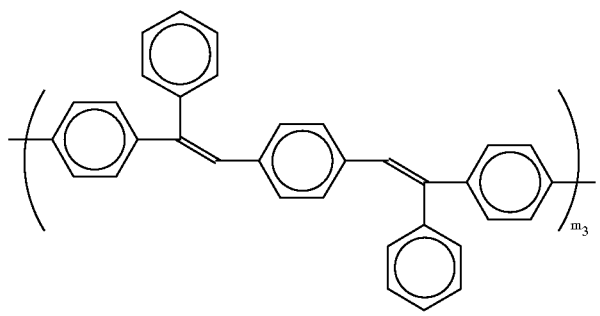
(4)
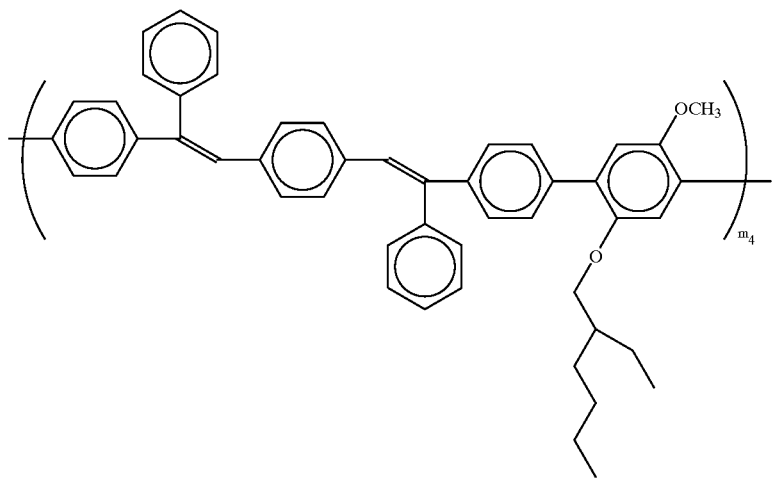
(5)
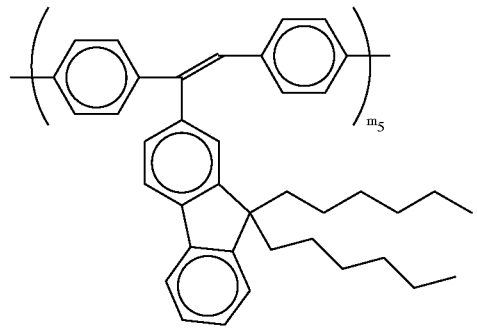
(6)

In the formulae (2) through (6), $m_1$, $m_2$, $m_3$, $m_4$ and $m_5$ are each integer from 10 to 200.

The compound represented by the formula (2) is the compound when $Ar_1$ and $Ar_6$ are single bonds; $Ar_2$ is represented by the following structural formula:

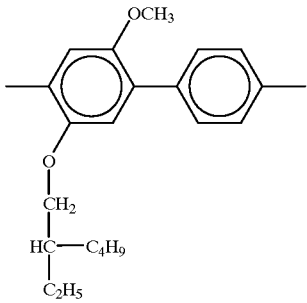

; l and k are 1; $Ar_4$ is represented by the following structural formula:

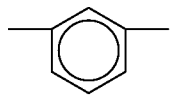

; $R_3$, $R_4$, $R_5$ and $R_6$ are all hydrogen; and $Ar_3$, $Ar_5$ and $Ar_7$ are all phenyl groups in the chemical formula (1).

The compound represented by the formula (3) is the compound when $Ar_3$ is a single bond; l and k are 0; $Ar_1$ is a biphenyl group; $Ar_2$ is a phenyl group and; $R_3$ and $R_4$ are all hydrogen in the chemical formula (1). The compound represented by the formula (4) is the compound when l and k are 1; $Ar_1$, $Ar_2$, $Ar_4$, $Ar_6$ and $Ar_7$ are all phenyl groups; $R_3$, $R_4$, $R_5$ and $R_6$ are all hydrogen; and $Ar_3$ and $Ar_5$ are single bonds. The compound represented by the formula (5) is the compound when $Ar_7$ is represented by the following structural formula:

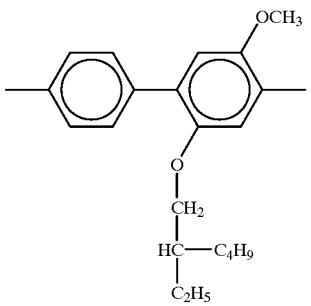

; $Ar_5$ is a single bond; $Ar_1$, $Ar_2$, $Ar_4$ and $Ar_6$ are all phenyl groups; $R_3$, $R_4$, $R_5$ and $R_6$ are all hydrogen; and l and k are 1 in the chemical formula (1). The compound represented by the formula (6) is the compound when $Ar_2$ is represented by the following structural formula:

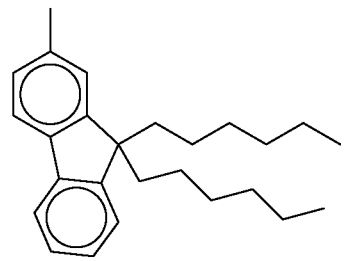

; $Ar_3$ is a single bond; $Ar_1$ and $Ar_4$ are all phenyl groups; $R_3$, $R_4$, $R_5$ and $R_6$ are all hydrogen; l is 1; and k is 0 in the chemical formula (1).

In particular, the compound of chemical formula (6) have dihexylfluorene group as $Ar_2$, the dihexylfluorne group hinders π-stacking between the compound and adjacent compound. If Such π-stacking is hindered, excitons can not be interacted each other. As a result, deterioration of luminous efficiency due to the interaction of excitons is prevented.

Preferably, the compound of the formula (1) according to the present invention has a molecular weight of $5 \times 10^3 \sim 2 \times 10^5$. This is because film characteristics are good in this molecular weight range of the compound of the formula (1).

Hereinafter, a method for manufacturing an organic EL device according to the present invention will be described.

First, a material for an anode is coated on a substrate. Here, the substrate is a substrate used for a general organic EL device, preferably, a glass substrate or a transparent plastic substrate which is good in transparency, surface flatness, convenience in handling and waterproofing characteristic. Also, indium tin oxide (ITO), tin oxide ($SnO_2$) or zinc oxide (ZnO), which is good in transparency and conductivity, is used as a material for the anode.

A material for forming a hole transport layer is spin-coated on the anode electrode, to form a hole transport layer. The compound of the formula (1) is spin-coated on the hole transport layer to form a light-emitting layer. A metal for forming a cathode is deposited under vacuum or spin-coated on the emitter layer, to form a cathode, thereby completing an organic EL device. Here, the material for the cathode may be lithium (Li), magnesium (Mg), aluminum (Al), an Al—Li alloy, calcium (Ca), a magnesium-indium (Mg—In) alloy or a magnesium-silver (Mg—Ag) alloy.

Here, an electron transport layer may be formed before the cathode is formed on the emitter layer. The electron transport layer is formed of a general material for an electron transport layer.

The material for the hole transport layer is not limited to a specific material. Preferably, the material for the hole transport layer is polyvinylcarbazole (PVK) or PDPMA reprsented by the following structural formula:

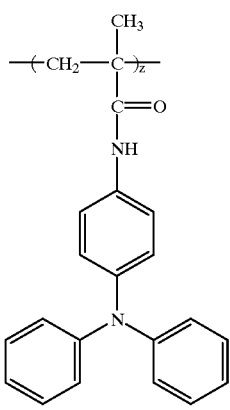

The organic EL device according to the present invention may further comprise an intermediate layer for improving characteristics of the device, between two layers selected from the anode, the hole transport layer, the emitter layer, the electron transport layer and the cathode. For example, a buffer layer may be formed between the anode and the hole transport layer. Such buffer layer decreases contact resistance between the anode and the hole transport layer, and simultaneously improves the transport ability of holes from the anode to the emitter layer, thereby improving overall characteristics of the device.

A material for the buffer layer is not limited to a specific material. However, preferably, the material for the buffer layer is polyethylene dioxythiophene (PEDT) or polyaniline.

The organic EL device is formed by stacking in sequence the anode, the hole transport layer, the emitter layer, the electron transport layer and the cathode as above. Alternatively, the order of stacking the respective layers may be reversed such that the cathode, the electron transport layer, the emitter layer, the hole transport layer and the anode are stacked in sequence.

FIGS. 2 through 5 illustrate the process of synthesizing the compounds represented by the formulae (2) through (5). Hereinafter, the present invention will be described in detail through the following examples with reference to FIGS. 2 and 5. However, the present invention is not limited to the following examples.

SYNTHESIS EXAMPLE 1

Compound of the Formula (2)

Aluminum chloride ($AlCl_3$) was added to an excessive amount of benzene contained in a round bottomed flask, and the mixture was cooled down in an ice bath. The resulting mixture was mixed with a solution obtained by dissolving isophthaloyl dichloride in benzene, and then reacted to attain a compound (A) (yield: 80%). The compound (A) was reacted with 4-bromobenzyl triphenyl phosphonium bromide for a Wittig reaction, resulting in a compound (B) (yield: 40%).

Dimethyl formamide (DMF), 2-ethylbromohexane and potassium carbonate ($K_2CO_3$) were added to 4-methoxyphenol, and the mixture was then refluxed for 24 hours.

The reaction mixture was poured in the cold water for precipitation. The resulting precipitate was filtered and dried to attain 2-(2'-ethylhexyloxy)-5-methoxy-benzene (C) (yield: 80%).

Benzene and bromine were added to 2-(2'-ethylhexyloxy)-5-methoxy-benzene (C) for bromination, resulting in 1,4-dibromo-2-(2'-ethylhexyloxy)-5-methoxybenzene (D) (yield: 65%).

Tetrahydrofuran (THF) and Mg were added to 1,4-dibromo-2-(2'-ethylhexyloxy)-5-methoxy-benzene (D) and refluxed for 1 hour, resulting in the corresponding Grinard reagent. The grinard reagent was reacted with trimethoxy borate to attain a compound (E) (yield: 47%).

THF, 2 mol of $K_2CO_3$ and tetrakis(triphenylphosphine) palladium were added to the compounds (B) and (E), and reacted for 24 hours, resulting in the compound represented by the formula (2) (yield: 85%). In the formula (2), $m_1$ was an integer from 10 to 200.

SYNTHESIS EXAMPLE 2

Compound of the Formula (3)

4-Bromobenzyl bromide was dissolved in benzene, 1 equiv. of triphenylphosphine was added to the solution and then refluxed for 12 hours to attain 4-bromobenzyl triphenyl phosphonium bromide (yield: 95%).

4-Bromoenzophenone was added to 4-bromobenzyl triphenyl phosphonium bromide for the Wittig reaction, to attain a compound (J) (yield: 40%).

Anhydrous nickel (II) chloride, 2,2'-bipyridine, triphenyl phosphine and zinc (Zn) power were put in a 3-neck round bottomed flask. The flask was purged with argon (Ar) gas about ten times.

Anhydrous DMF was added to the reaction mixture, and the temperature of the reaction mixture was controlled to 50° C. The compound (J) was rapidly added to the reaction mixture under nitrogen gas atmosphere, the temperature of the mixture was controlled to 90° C., and then the reaction mixture was stirred for 24 hours, resulting in the compound represented by the formula (3) (yield: 70%). In the formula (3), $m_2$ was an integer from 10 to 200.

SYNTHESIS EXAMPLE 3

Compound of the Formula (4)

α,α'-Dibromo-p-xylene was dissolved in DMF, and 2 equiv. of triphenylphosphine was added to the solution. Then, the mixture was refluxed for 12 hours to attain a compound (K) (yield: 90%).

2 Equiv. of 4-bromobenzophenol was added to the compound (K) for the Wittig reaction, resulting in a compound (L) (yield: 30%).

Anhydrous nickel (II) chloride, 2,2'-bipyridine, triphenyl phosphine and zinc (Zn) power were put in a 3-neck round bottomed flask. The flask was purged with argon (Ar) gas about ten times. Anhydrous DMF was added to the reaction mixture, and the temperature of the reaction mixture was controlled to 50° C. The compound (L) was rapidly added to the reaction mixture under nitrogen gas atmosphere, the temperature of the mixture was controlled to 90° C., and then the reaction mixture was stirred for 24 hours, resulting in the compound represented by the formula (4) (yield: 70%). In the formula (3), $m_3$ was an integer from 10 to 200.

SYNTHESIS EXAMPLE 4

Compound of the Formula (5)

4-Methoxy phenol was dissolved in DMF, and 2-ethylhexane and $K_2CO_3$ were added to the solution. Then, the mixture was refluxed for 24 hours.

The reaction mixture was poured in cold water for precipitation. The resulting precipitate was filtered and dried to attain a compound (M) (yield: 80%).

The compound (M) was dissolved in benzene, and 2 equiv. of bromine was added to the solution for bromination, to attain a compound (N) (yield: 65%).

The compound (N) was dissolved in THF, and Mg was added to the solution. The resulting mixture was refluxed for 1 hour, resulting in the corresponding Grinard reagent. Trimethyl borate was added to the Grinard reagent to attain 2-(2'-ethylhexyloxy)-5-methoxy-1,4-benzenediboronic acid (O) (yield: 47%).

α,α'-Dibromo-p-xylene was dissolved in DMF, and 2 equiv. of triphenylphosphine was added to the solution. The mixture was refluxed for 12 hours, to attain a compound (K) (yield: 90%).

4-Bromobenzophenone was added to the compound (K) for the Wittig reaction, resulting in a compound (L) (yield: 30%).

The compound (O) was dissolved in THF, and the compound (L), $K_2CO_3$(2M aqueous solution) and tetrakis(triphenylphosphine)palladium were added to the solution. Then, the mixture was reacted for 24 hours, resulting in the compound represented by the formula (5) (yield: 85%). In the formula (5), $m_4$ was an integer from 10 to 200.

EXAMPLE 1

After forming an electrode of ITO on a glass substrate, the compound of the formula (2) was spin-coated on the ITO electrode, to from a light-emitting layer having a thickness of 800 Å.

Then, Al and Li were simultaneously vapor-deposited under vacuum on the emitter layer, to form an Al—Li electrode having a thickness of 1,200 Å, resulting in an organic EL device.

EXAMPLE 2

An organic EL device was manufactured by the same method as in Example 1, except that the compound of the formula (3) was used instead of the compound of the formula (2) to form a light-emitting layer.

EXAMPLE 3

An organic EL device was manufactured by the same method as in Example 1, except that the compound of the formula (4) was used instead of the compound of the formula (2) to form a light-emitting layer.

EXAMPLE 4

After forming an electrode of ITO on a glass substrate, polyethylene dioxythiophene (PEDT) was spin-coated on the ITO electrode, to form a buffer layer having a thickness of 400 Å.

The compound of the formula (3) was spin-coated on the buffer layer to form a light-emitting layer having a thickness of 800 Å.

Then, Al and Li were simultaneously vapor-deposited under vacuum on the emitter layer, to form an Al—Li electrode having a thickness of 1,200 Å, resulting in an organic EL device.

EXAMPLE 5

PVK and the compound of the formula (3) was mixed in a mole ratio of 7:3, and the mixture was then dissolved in chlorobenzene to prepare a composition for a light-emitting layer. After forming an electrode of ITO on a glass substrate, the prepared composition was spin-coated on the ITO a light-emitting layer having a thickness of 800 Å.

Then, Al and Li were simultaneously vapor-deposited under vacuum on the emitter layer, to form an Al—Li electrode having a thickness of 1,200 Å, resulting in an organic EL device.

EXAMPLE 6

After forming an electrode of ITO on a glass substrate, a composition obtained by mixing PVK with the compound of the formula (3) in a mole ratio of 7:3 and dissolving the mixture in chlorobenzene was spin-coated on the ITO electrode to form a light-emitting layer having a thickness of 800 Å.

Tris(8-quinolinol) aluminum (Alq) represented by the following formula (7) was deposited under vacuum on the emitter layer to form an electron transport layer having a thickness of 200 Å.

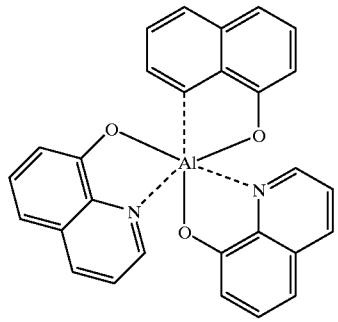

(7)

Then, Al and Li were simultaneously vapor-deposited under vacuum on the electron transport layer, to form an Al—Li electrode having a thickness of 1,200 Å, resulting in an organic EL device.

EXAMPLE 7

After forming an electrode of ITO on a glass substrate, PPV was spin-coated on the ITO electrode to form a hole transport layer having a thickness of 400 Å.

A composition obtained by mixing PVK with the compound of the formula (3) in a mole ratio of 7:3 and dissolving the mixture in chlorobenzene was spin-coated on the hole transport layer to form a light-emitting layer having a thickness of 800 Å.

Then, Al and Li were simultaneously vapor-deposited under vacuum on the emitter layer, to form an Al—Li electrode having a thickness of 1,200 Å, resulting in an organic EL device.

EXAMPLE 8

After forming an electrode of ITO on a glass substrate, PPV was spin-coated on the ITO electrode to form a hole transport layer having a thickness of 400 Å.

A composition obtained by mixing PVK with the compound of the formula (3) in a mole ratio of 7:3 and dissolving the mixture in chlorobenzene was spin-coated on the hole transport layer to form a light-emitting layer having a thickness of 800 Å.

Alq of the formula (7) was deposited under vacuum on the emitter layer to form an electron transport layer having a thickness of 200 Å.

Then, Al and Li were simultaneously vapor-deposited under vacuum on the electron transport layer, to form an Al—Li electrode having a thickness of 1,200 Å, resulting in an organic EL device.

EXAMPLE 9

After forming an electrode of ITO on a glass substrate, a composition obtained by mixing PVK with the compound of the formula (2) in a mole ratio of 1:1 and dissolving the mixture in chlorobenzene was spin-coated on the ITO electrode to form a light-emitting layer having a thickness of 800 Å.

Then, Al and Li were simultaneously vapor-deposited under vacuum on the emitter layer to form an Al—Li electrode having a thickness of 1,200 Å, resulting in an organic EL device.

EXAMPLE 10

After forming an electrode of ITO on a glass substrate, a composition obtained by mixing PVK with the compound of the formula (4) in a mole ratio of 1:1 and dissolving the mixture in chlorobenzene was spin-coated on the ITO electrode to form a light-emitting layer having a thickness of 800 Å.

Then, Al and Li were simultaneously vapor-deposited under vacuum on the light-emitting layer to form an Al—Li electrode having a thickness of 1,200 Å, resulting in an organic EL device.

EXAMPLE 11

After forming an electrode of ITO on a glass substrate, the compound of the formual (6) was spin-coated on the ITO electrode to form a light-emitting layer having a thickness of 1100 Å.

Then, Al and Li were simultaneously vapor-deposited under vacuum on the emitter layer to form an Al—Li electrode having a thickness of 1,300 Å, resulting in an organic EL device.

EXAMPLE 12

After forming an electrode of ITO on a glass substrate, a composition obtained by mixing PVK with the compound of the formula (6) in a mole ratio of 1:1 and dissolving the mixture in chlorobenzene was spin-coated on the ITO electrode to form a light-emitting layer having a thickness of 1100 Å.

Then, Al and Li were simultaneously vapor-deposited under vacuum on the light-emitting layer to form an Al—Li electrode having a thickness of 1,300 Å, resulting in an organic EL device.

Change in current density according to electric field strength, and emission spectra in the organic EL devices manufactured in Examples 1 through 12 are shown in FIGS. 6 through 20.

That is, FIGS. 6, 8, 9, 11, 12, 15, 17, 19 and 21 are graphs showing the change in current density according to voltage in the organic EL devices manufactured in Examples 1 through 12, and FIGS. 7, 10, 13, 14, 16, 18, 20 and 22 are graphs showing emission spectra of the organic electroluminescence (EL) devices manufactured in Examples 1, 3, 5, 6, 7, 8, 9, 10, 11 and 12.

Figure 12:
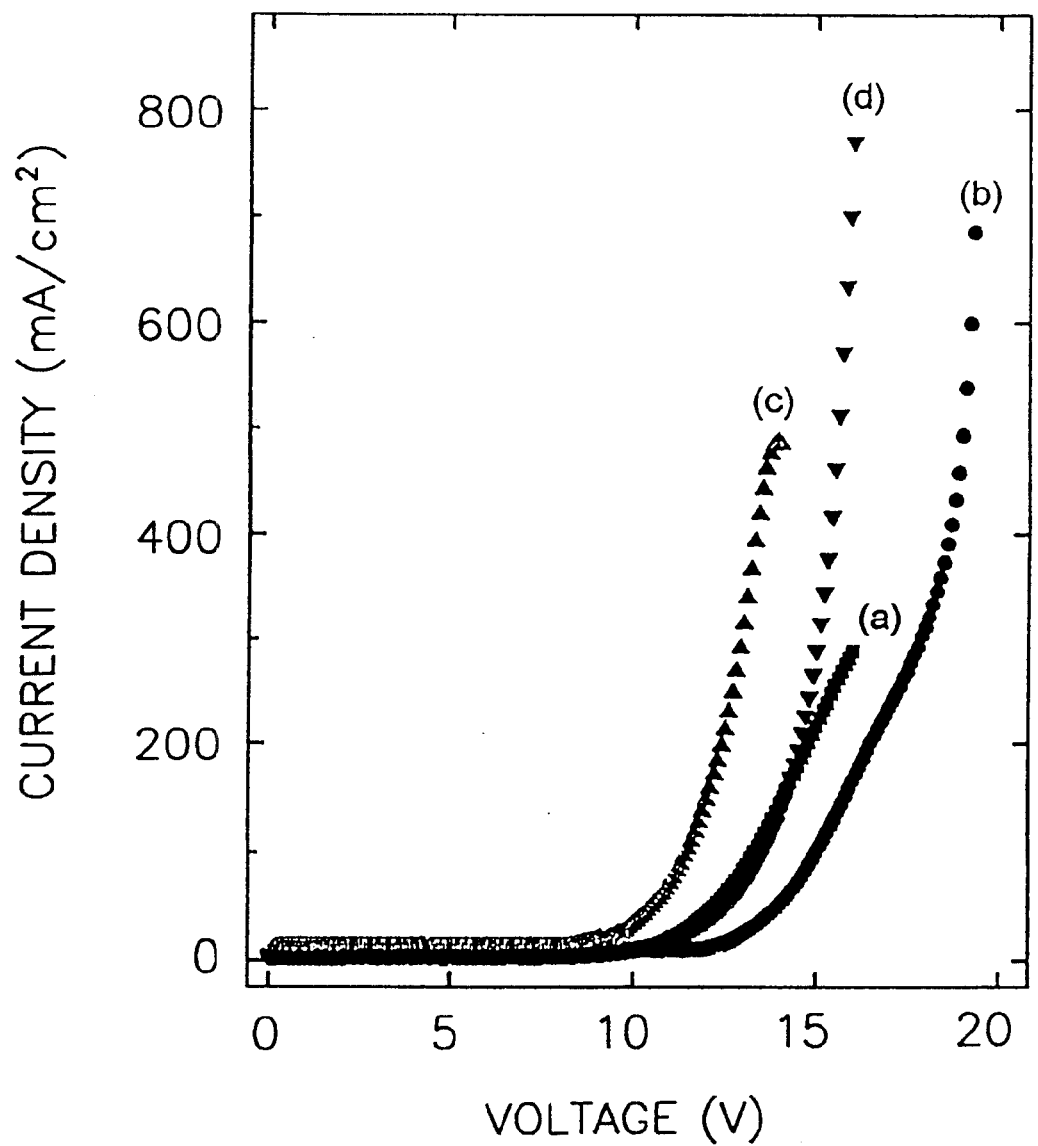
Figure 13:
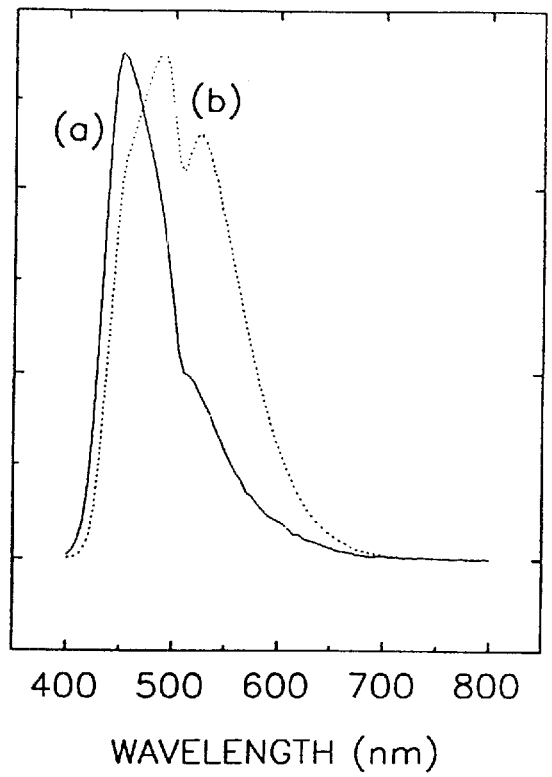
Figure 14:
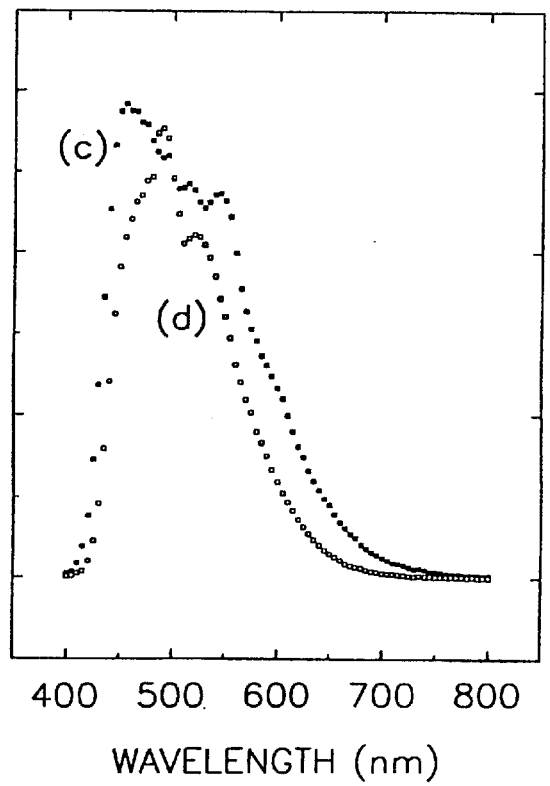
Figure 15:
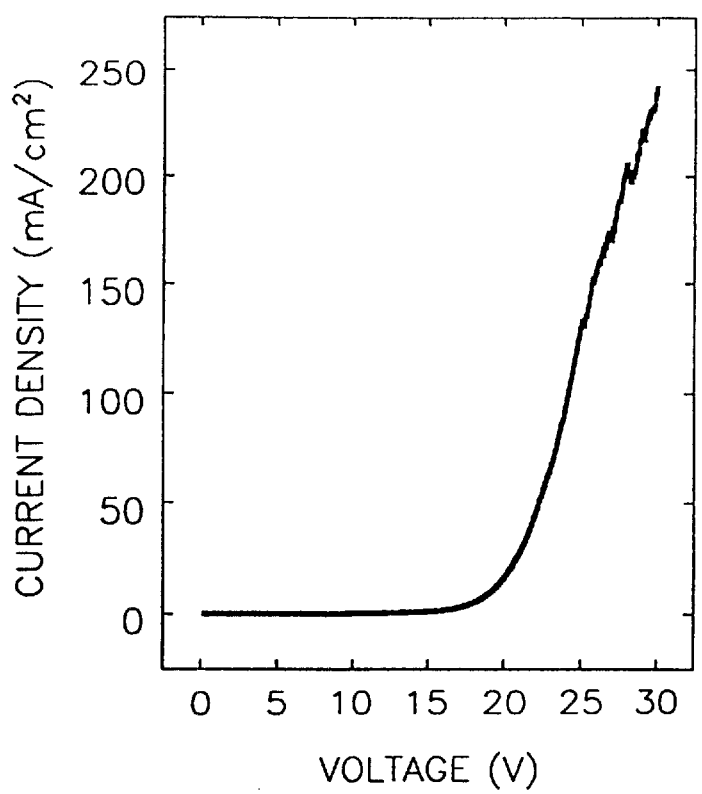
Figure 16:
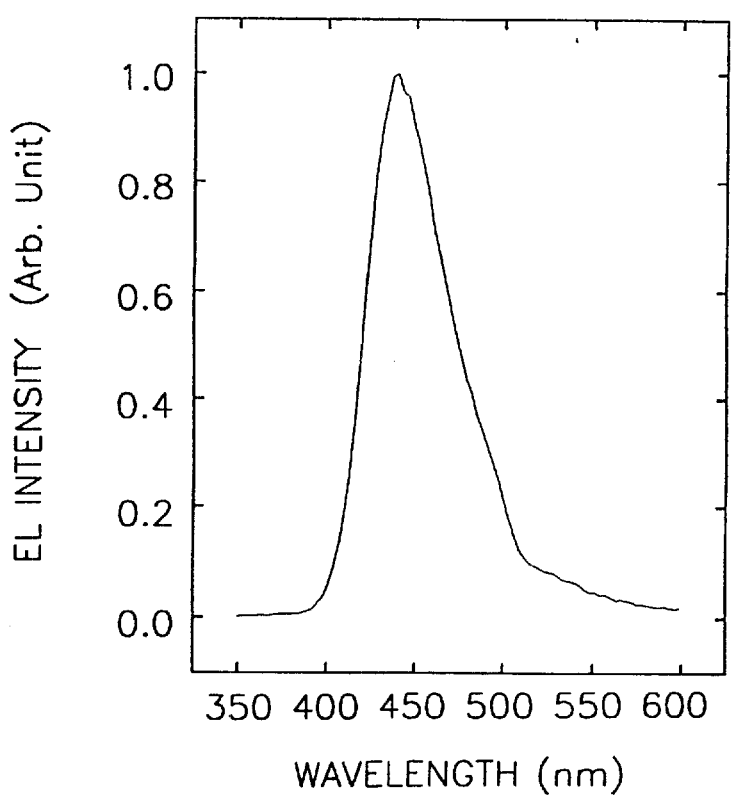
Figure 17:
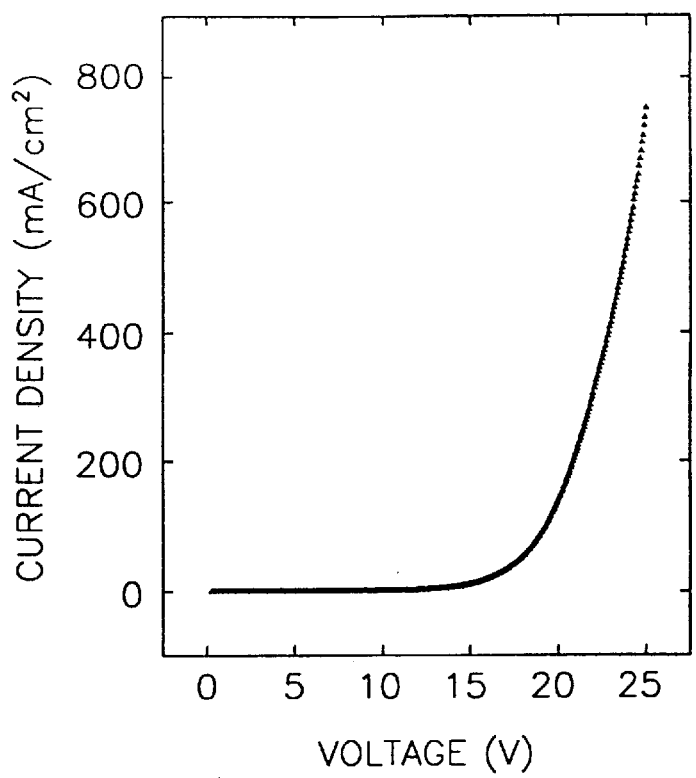
Figure 18:
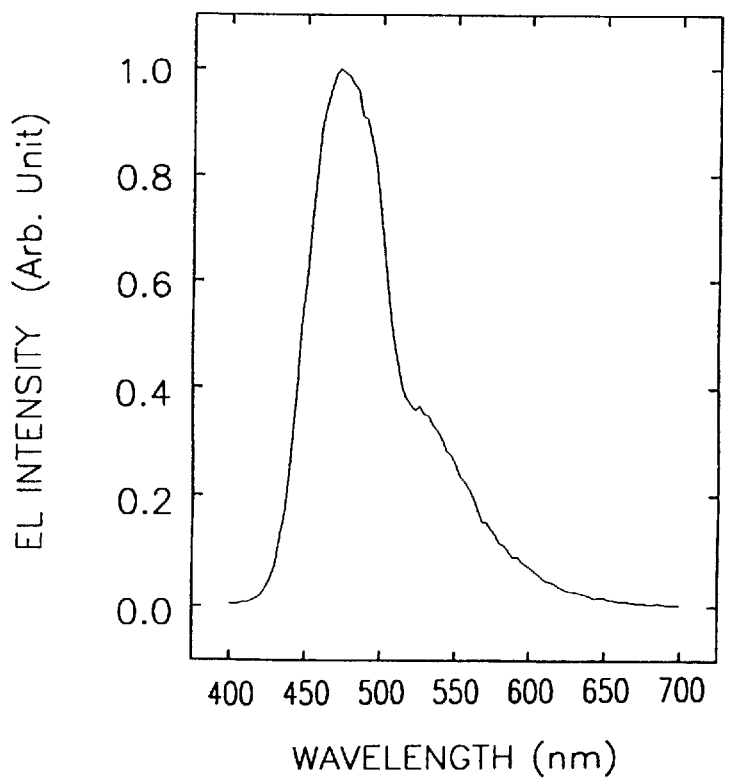
Figure 19:
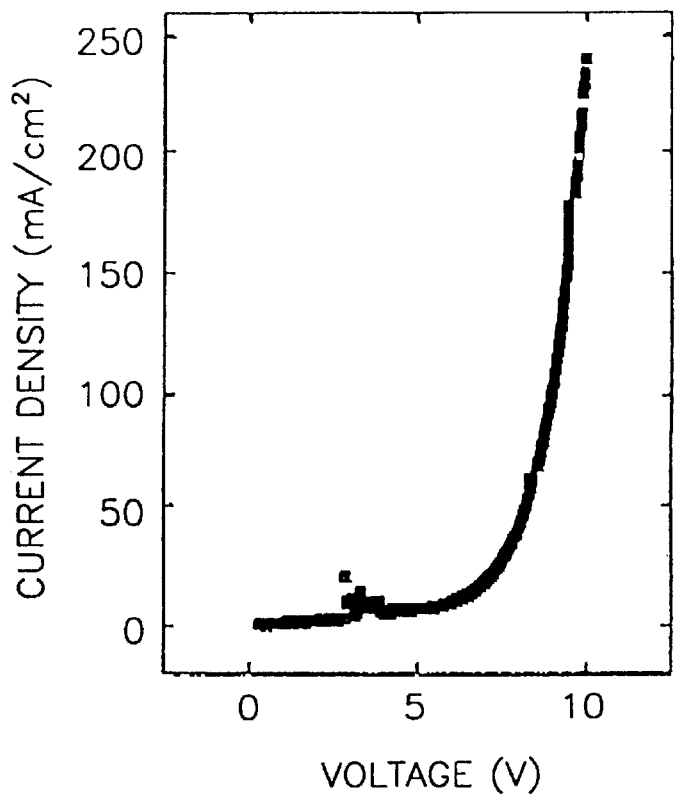
Figure 20:
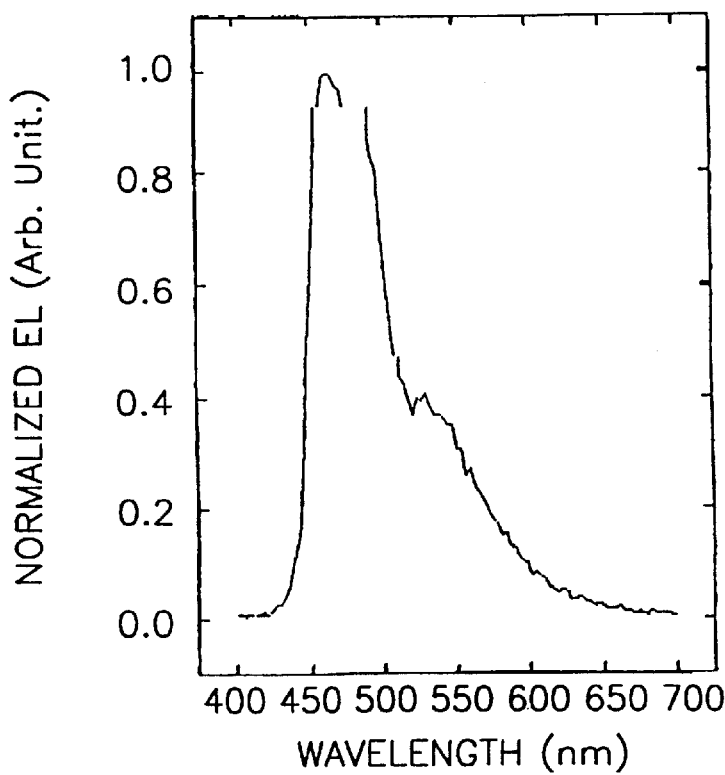
Figure 21:
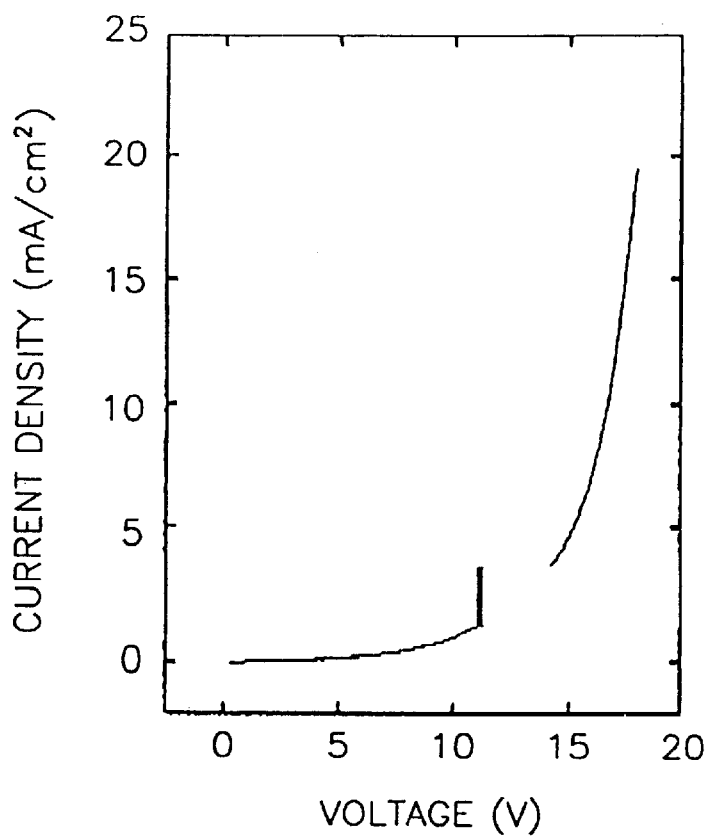
Figure 22:
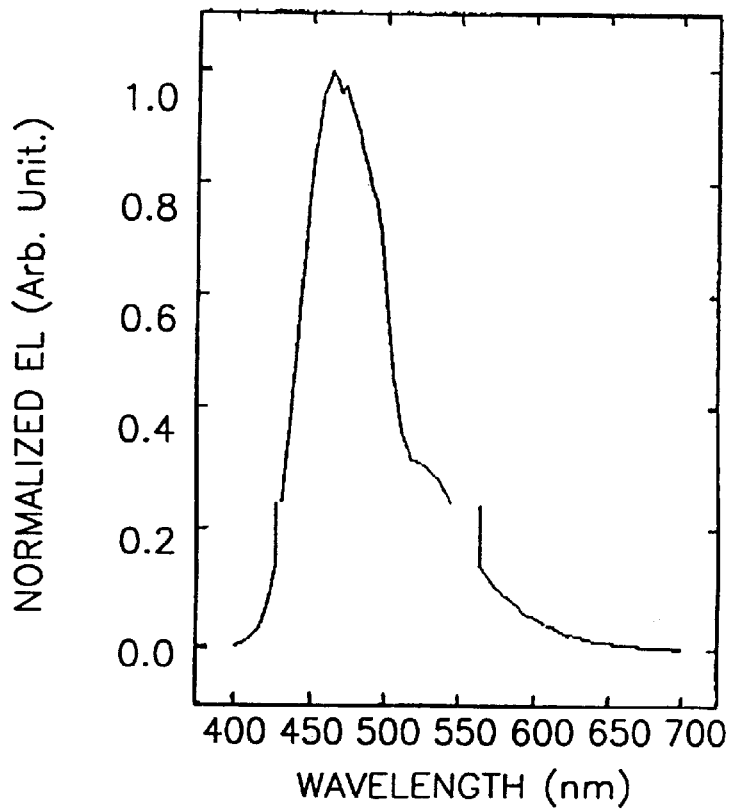

In FIG. 12, which is a graph showing the changes in current density according to the voltage, lines (a), (b), (c) and (d) are of Examples 5, 6, 7 and 8, respectively. In FIG. 13, line (a) represents the emission spectrum of the organic EL device manufactured in Example 5, and line (b) represents the emission spectrum of the organic EL device manufactured in Example 6, respectively. In FIG. 14, line (c) represents the emission spectrum of the organic EL device of Examle 7 and line (d) represents the emission spectrum of the organic EL device of Example 8.

Turn-on voltage, luminance and color characteristics of the organic EL devices manufactured in Examples 1 through 10 were measured based on FIGS. 6 through 20, and the results are tabulated in Table 1.

TABLE 1

| classification | turn-on voltage (V) | luminance (cd/m$^2$) | color (EL λ max) |
| --- | --- | --- | --- |
| Example 1 | 10 | 50 | blue |
| Example 2 | 12 | 150 | blue |
| Example 3 | 9 | 300 | bluish-white |
| Example 4 | 8 | 200 | blue |
| Example 5 | 11 | 1000 | blue |
| Example 6 | 13 | 1700 | bluish-white |
| Example 7 | 9 | 1500 | bluish-white |
| Example 8 | 12 | 1200 | bluish-white |
| Example 9 | 15 | 100 | blue |
| Example 10 | 16 | 1200 | blue |
| Example 11 | 8 | 100 | blue |
| Example 12 | 10 | 700 | blue |

As can be understood from Table 1, the organic EL devices manufactured in Examples 1 through 12 are improved in luminance and driving voltage characteristics compared to the case of using a general blue light-emitting material, such that it can display blue or bluish-white.

The light-emitting compound of the formula (1) according to the present invention, as a blue light-emitting material, is useful as a color-developing material for a display. The organic EL device according to the present invention, adopting an organic layer formed of such light-emitting compound, can display blue and have good luminous efficiency.

What is claimed is:

1. A light-emitting compound represented by the chemical formula (1):

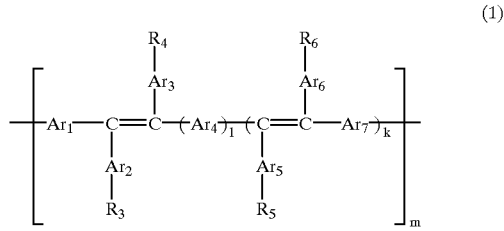

(1)

wherein $Ar_1$, $Ar_2$, $Ar_3$, $Ar_5$, $Ar_6$ and $Ar_7$ are independtly selected from the group consisting of chemical bond, unsubstituted or substituted phenyl, unsubstituted or substituted naphthalene, unsubstituted or substituted anthracene, unsubstituted or substituted diphenylanthracene, unsubstituted or substituted phenanthrene, unsubstituted or substituted indene, unsubstituted or substituted acenaphtene, unsubstituted or substituted biphenyl, unsubstituted or substituted fluorene, unsubstituted or substituted carbazole, unsubstituted or substituted thiophene, unsubstituted or substituted pyridine, unsubstituted or substituted oxadiazole, unsubstituted or substituted oxazole, unsubstituted or substituted triazole, unsubstituted or substituted benzothiophene, unsubstituted or substituted dibenzofuran, and unsubstituted or substituted thiadiazole; $Ar_4$ is selected from the group consisting of unsubstituted or substituted phenyl, unsubstituted or substituted biphenyl, unsubstituted or substituted thiophene, unsubstituted or substituted pyridine, unsubstituted or substituted oxadiazole, unsubstituted or substituted oxazole, unsubstituted or substituted triazole, and unsubstituted or substituted thiadiazole; $R_1$, $R_2$, $R_3$, $R_4$, $R_5$ and $R_6$ are independently selected from the group consisting of hydrogen, ethyleneoxyalkyl group, $C_1$–$C_{20}$ alkyl group, $C_1$–$C_{20}$ alkoxy group, aryl group, trimethylsilyl group, and trimethylsilylaryl group; l and k are independently 0 or 1; and m is an integer from 10 to 200.

2. The light-emitting compound of claim 1, wherein $Ar_1$ is represented by the following structural formula:

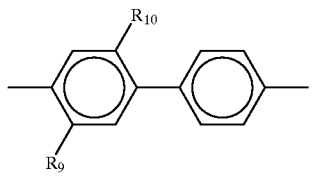

; $R_9$ and $R_{10}$ are independently a $C_1$–$C_{20}$ alkyl group or $C_1$–$C_{20}$ alkoxy group.

3. The light-emitting compound of claim 1, wherein $Ar_7$ is represented by the following structural formula:

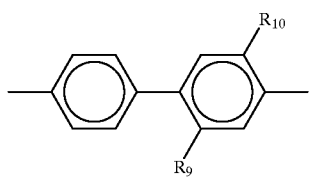

; $R_9$ and $R_{10}$ are independently a $C_1$–$C_{20}$ alkyl group or $C_1$–$C_{20}$ alkoxy group.

4. The light-emitting compound of claim 1, wherein $Ar_2$ is represented by the following structural formula:

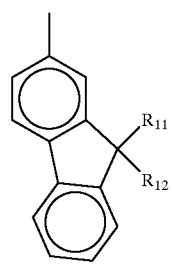

; $R_{11}$ and $R_{12}$ are independently a $C_1$–$C_{20}$ alkyl group, phenyl group or alkylsilyl group.

5. The light-emitting compound of claim 1, wherein molecular weight of the compound is $5 \times 10^3 \sim 2 \times 10^5$.

6. The light-emitting compound of claim 1, wherein $Ar_1$ and $Ar_6$ are single bonds; $Ar_2$ is represented by the following structural formula:

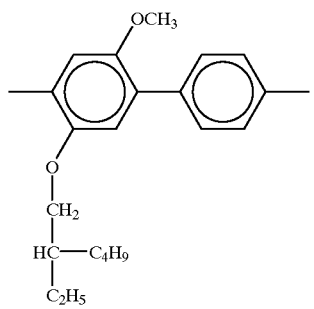

; l and k are 1; $Ar_4$ is represented by the following structural formula:

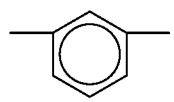

; $R_3$, $R_4$, $R_5$ and $R_6$ are all hydrogen; and $Ar_3$, $Ar_5$ and $Ar_7$ are all phenyl groups.

7. The light-emitting compound of claim 1, wherein $Ar_3$ is a single bond; l and k are 0; $Ar_1$ is a biphenyl group; $Ar_2$ is a phenyl group and; $R_3$ and $R_4$ are all hydrogen.

8. The light-emitting compound of claim 1, wherein l and k are 1; $Ar_1$, $Ar_2$, $Ar_4$, $Ar_6$ and $Ar_7$ are all phenyl groups; $R_3$, $R_4$, $R_5$ and $R_6$ are all hydrogen; and $Ar_3$ and $Ar_5$ are single bonds.

9. The light-emitting compound of claim 1, wherein $Ar_7$ is represented by the following structural formula:

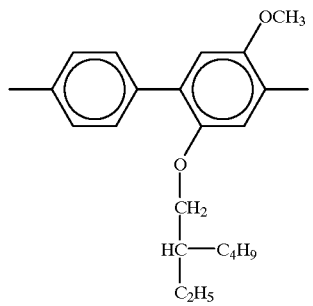

; $Ar_5$ is a single bond; $Ar_1$, $Ar_2$, $Ar_4$ and $Ar_6$ are all phenyl groups; $R_3$, $R_4$, $R_5$ and $R_6$ are all hydrogen; and l and k are 1.

10. The light-emitting compound of claim 1, wherein $Ar_2$ is represented by the following structural formula:

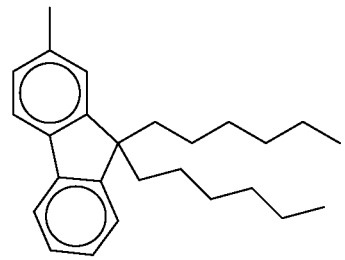

; $Ar_3$ is a single bond; $Ar_1$ and $Ar_4$ are all phenyl groups; $R_3$, $R_4$, $R_5$ and $R_6$ are all hydrogen; l is 1; and k is 0.

11. An organic electro-luminescence device comprising an organic layer between a pair of electrodes, wherein the organic layer comprises a light-emitting compound represented by the chemical formula (1):

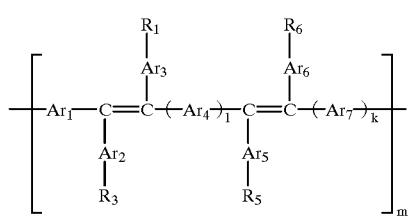

(1)

wherein $Ar_1$, $Ar_2$, $Ar_3$, $Ar_5$, $Ar_6$ and $Ar_7$ are independtly selected from the 9 group consisting of chemical bond, unsubstituted or substituted phenyl, unsubstituted or substituted naphthalene, unsubstituted or substituted anthracene, unsubstituted or substituted diphenylanthracene, unsubstituted or substituted phenanthrene, unsubstituted or substituted indene, unsubstituted or substituted acenaphtene, unsubstituted or substituted biphenyl, unsubstituted or substituted fluorene, unsubstituted or substituted carbazole, unsubstituted or substituted thiophene, unsubstituted or substituted pyridine, unsubstituted or substituted oxadiazole, unsubstituted or substituted oxazole, unsubstituted or substituted triazole, unsubstituted or substituted benzothiophene, unsubstituted or substituted dibenzofuran, and unsubstituted or substituted thiadiazole; $Ar_4$ is selected from the group consisting of unsubstituted or substituted phenyl, unsubstituted or substituted biphenyl, unsubstituted or substituted thiophene, unsubstituted or substituted pyridine, unsubstituted or substituted oxadiazole, unsubstituted or substituted oxazole, unsubstituted or substituted triazole, and unsubstituted or substituted thiadiazole; $R_1$, $R_2$, $R_3$, $R_4$, $R_5$ and $R_6$ are independently selected from the group consisting of hydrogen, ethyleneoxyalkyl group, $C_1$–$C_{20}$ alkyl group, $C_1$–$C_{20}$ alkoxy group, aryl group, trimethylsilyl group, and trimethylsilylaryl group; l and k are independently 0 or 1; and m is an integer from 10 to 200.

12. The organic electro-luminescence device of claim 11, wherein $Ar_1$ is represented by the following structural formula:

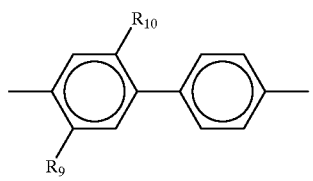

; $R_9$ and $R_{10}$ are independently a $C_1$–$C_{20}$ alkyl group or $C_1$–$C_{20}$ alkoxy group.

13. The organic electro-luminescence device of claim 11, wherein $Ar_7$ is represented by the following structural formula:

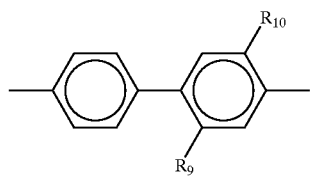

; $R_9$ and $R_{10}$ are independently a $C_1$–$C_{20}$ alkyl group or $C_1$–$C_{20}$ alkoxy group.

14. The organic electro-luminescence device of claim 11, $Ar_2$ is represented by the following structural formula:

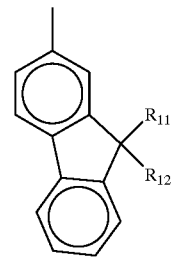

; $R_{11}$ and $R_{12}$ are independently a $C_1$–$C_{20}$ alkyl group, phenyl group or alkylsilyl group.

15. The organic electro-luminescence device of claim 11, wherein molecular weight of the compound is $5 \times 10^3 \sim 2 \times 10^5$.

16. The organic electro-luminescence device of claim 11, wherein $Ar_1$ and $Ar_6$ are single bonds; $Ar_2$ is represented by the following structural formula:

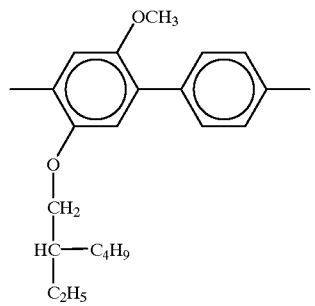

; l and k are 1; $Ar_4$ is represented by the following structural formula:

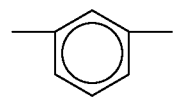

; $R_3$, $R_4$, $R_5$ and $R_6$ are all hydrogen; and $Ar_3$, $Ar_5$ and $Ar_7$ are all phenyl groups.

17. The organic electro-luminescence device of claim 11, wherein $Ar_3$ is a single bond; l and k are 0; $Ar_1$ is a biphenyl group; $Ar_2$ is a phenyl group and; $R_3$ and $R_4$ are all hydrogen.

18. The organic electro-luminescence device of claim 11, wherein l and k are 1; $Ar_1$, $Ar_2$, $Ar_4$, $Ar_6$ and $Ar_7$ are all phenyl groups; $R_3$, $R_4$, $R_5$ and $R_6$ are all hydrogen; and $Ar_3$ and $Ar_5$ are single bonds.

19. The organic electro-luminescence device of claim 11, wherein $Ar_7$ is represented by the following structural formula:

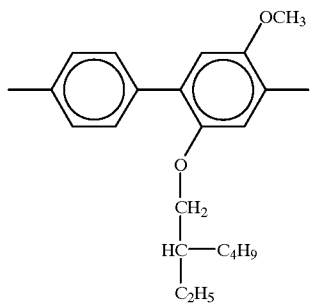

; $Ar_5$ is a single bond; $Ar_1$, $Ar_2$, $Ar_4$ and $Ar_6$ are all phenyl groups; $R_3$, $R_4$, $R_5$ and $R_6$ are all hydrogen; and l and k are 1.

20. The organic electro-luminescence device of claim 1, wherein $Ar_2$ is represented by the following structural formula:

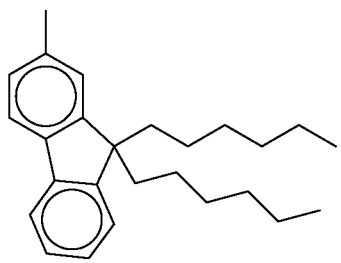

; $Ar_3$ is a single bond; $Ar_1$ and $Ar_4$ are all phenyl groups; $R_3$, $R_4$, $R_5$ and $R_6$ are all hydrogen; l is 1; and k is 0.

21. The organic electro-luminescence device of claim 9, wherein the organic layer is a light-emitting layer or an electron transport layer.

22. A display device adopting the light-emitting compound claimed in 1 as a color-developing substance.

* * * * *